(12) United States Patent
Kellogg

(10) Patent No.: US 10,130,947 B2
(45) Date of Patent: Nov. 20, 2018

(54) VALVING SYSTEM FOR USE IN CENTRIFUGAL MICROFLUIDIC PLATFORMS

(71) Applicant: Radisens Diagnostics Limited, Cork (IE)

(72) Inventor: Gregory J. Kellogg, Cambridge, MA (US)

(73) Assignee: Radisens Diagnostics Limited, Cork (IE)

( * ) Notice: Subject to any disclaimer, the term of this patent is extended or adjusted under 35 U.S.C. 154(b) by 0 days.

(21) Appl. No.: 14/649,654

(22) PCT Filed: Dec. 5, 2013

(86) PCT No.: PCT/EP2013/075736
§ 371 (c)(1),
(2) Date: Jun. 4, 2015

(87) PCT Pub. No.: WO2014/086956
PCT Pub. Date: Jun. 12, 2014

(65) Prior Publication Data
US 2015/0314289 A1    Nov. 5, 2015

Related U.S. Application Data

(60) Provisional application No. 61/733,866, filed on Dec. 5, 2012.

(30) Foreign Application Priority Data

Dec. 5, 2012   (EP) .................................... 12195761

(51) Int. Cl.
*B01L 3/00* (2006.01)
*F16K 99/00* (2006.01)
*G01N 33/49* (2006.01)

(52) U.S. Cl.
CPC ... *B01L 3/502738* (2013.01); *B01L 3/502761* (2013.01); *F16K 99/0063* (2013.01);
(Continued)

(58) Field of Classification Search
CPC .. B01L 3/502738; B01L 3/5027; B01L 3/502; B01L 3/50
(Continued)

(56) References Cited

U.S. PATENT DOCUMENTS 5,693,233 A    12/1997  Schembri
6,063,589 A *   5/2000  Kellogg .............. B01F 13/0059
                                         366/DIG. 3
(Continued)

FOREIGN PATENT DOCUMENTS

WO         02/074438 A2     9/2002
WO    WO 2012/164552 A1 *  12/2012  ........... G01N 33/543

OTHER PUBLICATIONS

PCT Written Opinion for PCT International Patent Application No. PCT/EP2013/075736, dated Jun. 15, 2014 (9 pages).
Gorkin, Robert et al., "Centifugal microfluidics for biomedical applications", The Royal Society of Chemistry, Lab Chip, vol. 10, (2010), pp. 1758-1773.

*Primary Examiner* — Christine T Mui
(74) *Attorney, Agent, or Firm* — K&L Gates LLP

(57) ABSTRACT

The invention relates to a microfluidic system for processing biological samples comprising a holding chamber adapted for holding a fluid and to be rotated on a platform, said holding chamber comprising an outlet through which fluid flow is controlled by an acceleration-primed valve system, wherein the acceleration-primed valve system comprises a capillary valve and an outlet channel. The invention provides a novel valving system, which retains fluids at low angular velocities, removes the need for hydrophilic surfaces, minimizes disc real-estate and optimizes certain microfluidic processes done in the holding chamber.

14 Claims, 2 Drawing Sheets

(52) U.S. Cl.
CPC ........ *G01N 33/491* (2013.01); *B01L 2200/06* (2013.01); *B01L 2200/0652* (2013.01); *B01L 2200/0668* (2013.01); *B01L 2200/10* (2013.01); *B01L 2300/0806* (2013.01); *B01L 2300/087* (2013.01); *B01L 2300/088* (2013.01); *B01L 2300/0848* (2013.01); *B01L 2300/0864* (2013.01); *B01L 2300/0887* (2013.01); *B01L 2300/161* (2013.01); *B01L 2400/0406* (2013.01); *B01L 2400/0409* (2013.01); *B01L 2400/0688* (2013.01); *F16K 2099/0084* (2013.01)

(58) Field of Classification Search
USPC .................. 422/506, 504, 502, 501, 500, 50
See application file for complete search history.

(56) References Cited

U.S. PATENT DOCUMENTS

| | | | |
|---|---|---|---|
| 6,143,248 | A | 11/2000 | Kellogg et al. |
| 6,632,399 | B1 | 10/2003 | Kellogg et al. |
| 2004/0089616 | A1* | 5/2004 | Kellogg .............. B01F 13/0059 210/749 |
| 2004/0209374 | A1 | 10/2004 | Kopf-Sill et al. |
| 2007/0003437 | A1 | 1/2007 | Ozaki et al. |
| 2011/0094600 | A1 | 4/2011 | Bergeron et al. |
| 2011/0111987 | A1 | 5/2011 | Siegrist et al. |

\* cited by examiner

VALVING SYSTEM FOR USE IN CENTRIFUGAL MICROFLUIDIC PLATFORMS

CROSS REFERENCE TO RELATED APPLICATIONS

This is the national phase under 35 U.S.C. § 371 of International Application No. PCT/EP2013/075736 filed on Dec. 5, 2013, which claims priority to and benefit of European Patent Application No. 12195761.7 filed on Dec. 5, 2012 and U.S. Provisional Ser. No. 61/733,866 filed on Dec. 5, 2012, the entire disclosures of each of which are incorporated by reference herein.

FIELD

The invention relates to a new valving system related to a microfluidic disc, apparatus, system and method, for use in clinical diagnostics. In particular the invention relates to an acceleration-Primed valving system for use in centrifugal Microfluidic Platforms.

BACKGROUND

Manual processing to determine the cellular/biological content of various types of samples, and in particular samples that contain living cells, is cost-prohibitive in many applications and is also prone to errors. Automation is also cost-prohibitive in many applications, and is inappropriate as currently practiced—using, for example, liquid handling robots—for applications such as point-of-care or doctor's office analysis. As a result, there is an unmet need to provide sample processing for multiplexed biological assays that is less expensive and less prone to error than current automation or manual processing.

Certain Point-of-Care diagnostic assay systems based on centrifugal microfluidic technology are quite good at performing the necessary integrated sample preparation and assay measurement steps. This centrifugal microfluidic platform with optical detection allows for a variety of assay technologies to be implemented in parallel using a single instrument and disposable suite.

Gating or valving of liquids is a key feature of most centrifugal fluidic platforms, with a variety of different such means existing. These include but not limited to the use of siphoning; passive single-use valves based on surface tension effects (capillary valves, hydrophobic valves); single-use valves based on solid-to-liquid phase transition or melting of a "plug" due to heat applied by a contact heater or light source; and multiple-use valves based on the same principals. Some of these valving mechanisms are well known in the art and have entered the public domain, as described in U.S. Pat. No. 5,693,233, Abaxis.

It is recognized in the art, such as U.S. Pat. No. 6,143,248, Camera, that manipulation of liquid properties (surface tension, density), material properties (contact angle); and geometric parameters such as the capillary dimensions and configuration of the fluids on the disc; results in well-defined rotational velocities at which capillary pressure is 'defeated' and liquid 'bursts' through passive valves. Using these relationships, a wide range of relevant biological fluids and reagents may be gated at rotational rates from a few hundred RPM (revolutions per minute) to more than 5000 RPM. Siphons function in this way: A chamber is provided by an outlet channel which proceeds radially inward from the chamber and whose path doubles backwards, forming a U, and thus points radially outward. The "U" of the channel is at a radius inward of where the liquid meniscus of the defined volume of liquid which is to be resident in the chamber when the disc is under rotation. In this way, liquid does not proceed through the siphon at high rotational velocities.

As rotational velocity is decreased, capillary action may be used to imbibe the liquid within the siphon. The liquid is drawn past the U, until the liquid meniscus is at a point radially-outward of the position of the radially-inward meniscus of liquid filling the chamber. Upon increased rotational velocity, the meniscus in the channel acts to "pull" liquid from the chamber, just as liquid in a siphon under the influence of gravity may be used to empty a container by first rising above the container surface, and then dropping below it. The container will be emptied completely if the outlet of the channel is below the lowermost portion of the container. In the same way, the siphon on a centrifugal disc can be seen to function.

Siphons are useful because they act in an opposite fashion from capillary valves: Fluid will not flow past a siphon at a high rotational speed, unless the velocity is first decreased to allow capillary action to occur. This is especially useful for high velocity separation processes such as separation from plasma from whole blood, where the separation time is minimized if the rotational velocity is maximized. As a result, it is desirable to have valves at various points in the process which will not allow flow, no matter how great the rotational speed.

US 2004/0209374, Abaxis, requires that the location of the inner radial bend of a siphon is located closer to the centre than the holding structure that feeds it. This design relies on a smooth and hydrophilic surface to enable capillary action defeat the valve. US 2011/0094600, Bergeron et al, refer to standard siphons in the art and introduces a serial siphon valve design.

PCT Patent publication number WO02/074438, assigned to Gyros AB, discloses a microfluidic device that comprises several microchannel structures. A paper published by Gorkin et al 'Centrifugal microfluidics for biomedical applications' Lab on a Chip, Royal Society of Chemistry, col. 10, 28 May 2010, Pages 1758-1773 discloses a centrifugal microfluidic platform for biomedical applications having a siphon having a hydrophilic surface. A problem with siphons described in the art is that liquids cannot be retained within the chamber at low rotational velocities. For example, if the chamber is to be used for an incubation step where slow agitations are required, the meniscus may be drawn by capillary action around the "U" and the chamber emptied upon acceleration of the disc. Similarly, if a detection step is required where the disc must be stationary, the siphon will be defeated.

A further problem is the necessity for capillary action. This typically requires that the surface of the channel be smooth and hydrophilic. The latter is usually accomplished by surface treatment, e.g., plasma etching or deposition of hydrophilic materials. This adds to the costs and complexities of disc manufacture.

It is therefore an object of this invention to provide a valving system for use on a centrifugal microfluidic platform to overcome at least one of the above mentioned problems.

SUMMARY OF THE INVENTION

According to the invention there is provided, as set out in the appended claims, a microfluidic system for processing biological samples comprising:
  a holding chamber adapted for holding a fluid and to be rotated on a platform, said holding chamber comprising an outlet through which fluid flow is controlled by an acceleration-primed valve system, wherein the acceleration-primed valve system comprises a capillary valve and an outlet channel.

The invention provides a valving system, which retains fluids at low angular velocities, removes the need for hydrophilic surfaces, minimises disc real-estate and optimises certain microfluidic processes done in the holding chamber.

The invention provides an acceleration-primed valve, comprising an acceleration-primed valve and a capillary valve in a particular embodiment with a means for closing and opening the acceleration-primed valve system.

In one embodiment the holding chamber is dimensioned to have an inner radial wall of radius R1 and outer radial wall of radius R2 from the central axis, and the capillary valve comprises an innermost portion that is radially outward, R3, of the innermost portion of the holding chamber, R1.

In one embodiment on rotating the platform about the axis at a first speed the fluid in the holding chamber is pushed against the capillary valve at the radius R3 such that the fluid remains in the holding chamber.

In one embodiment the platform is adapted to be rotated at a second speed such that the tangential acceleration is chosen such that the induced pressure transient is greater than the release pressure of the capillary valve to enable fluid flow to the outlet channel.

In one embodiment there is provided means for opening the capillary valve by applying sufficient rotation speed to the platform.

In one embodiment the outlet channel extends radially inwardly and having an innermost portion that is radially outward of the innermost portion of the holding chamber.

In one embodiment the outlet channel is dimensioned in a substantially goose-neck type shape.

In one embodiment the outlet channel comprises a hydrophilic capillary channel adapted to allow the fluid from the holding chamber to flow into the outlet channel via capillary force, when the capillary valve is opened.

In one embodiment the fluid is allowed to flow into the outlet channel by reducing the angular velocity of the platform to a speed such that the capillary force within the outlet channel is greater than centrifugal force exerted on the holding chamber.

In one embodiment a second capillary valve is adapted to allow delivery of fluid at a time controlled by an angular velocity high enough to open the output capillary valve.

In another embodiment there is provided a microfluidic system for processing biological samples comprising:
 a holding chamber adapted for holding a fluid and to be rotated on a platform, said holding chamber comprising an outlet through which fluid flow is controlled by an acceleration-primed valve system, wherein the acceleration-primed valve system comprises a valve and an outlet channel. In this embodiment capillary action is not required and the fluid can travel via the output channel if sufficient force generated by acceleration is applied when the platform is rotated.

It will be appreciated that centrifugal force can be used to pump once the valve/outlet channel has been primed by a force generated by one or more accelerations.

In a further embodiment of the invention there is provided a microfluidic system for separating plasma within whole blood comprising:
 a platform coupled to a rotary motor;
 a plasma holding chamber connected to a cell holding chamber radially outward of it, wherein said connection comprises a plurality of transport capillary channels.

In one embodiment at least one of the transport capillaries is adapted to dampen down agitated cells in the blood limiting their resuspension into the plasma holding chamber.

In one embodiment said structure is used for the separation of any particles in solution.

For cases where the surface is hydrophobic, siphons do not prime as described in the art. This acceleration-primed valve is primed through rapid acceleration, generating a pressure pulse that primes the acceleration-primed valve or defeats capillary valves, based on the following steps:
1. Centrifugation to high speed breaks a retaining capillary valve that prevents premature filling of the acceleration-primed valve from the holding chamber at lower rotational speeds.
2. Centrifugation continues at max speed of system without flow of sample to receiving chamber.
3. Reduce RPM: capillary action draws liquid into the acceleration-primed valve, as capillary valve already defeated
4. Increase RPM: liquid distributed to receiving chamber.

BRIEF DESCRIPTION OF THE DRAWINGS

The invention will be more clearly understood from the following description of an embodiment thereof, given by way of example only, with reference to the accompanying drawings, in which:—

DETAILED DESCRIPTION OF THE INVENTION

Figure 1:
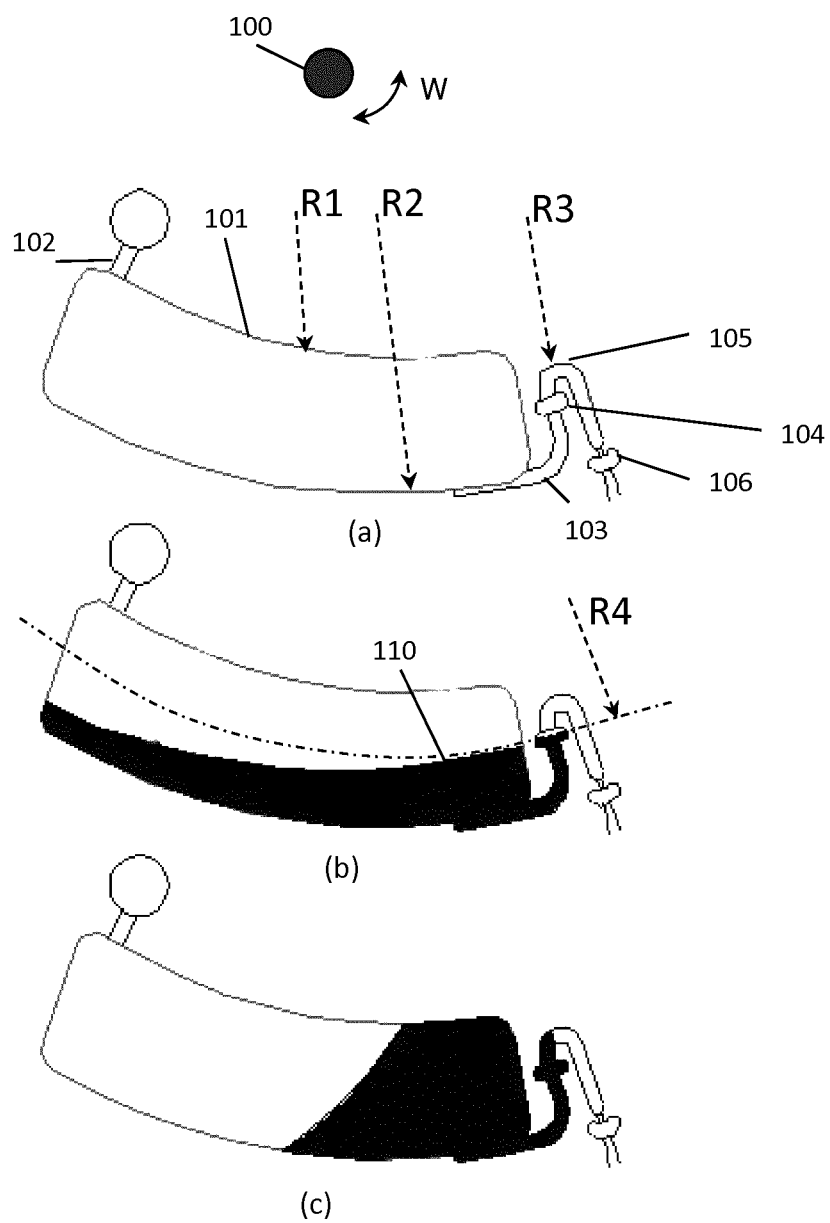
FIG. 1 presents a platform structure with a holding chamber, with fluid flow through an output channel controlled via an acceleration-primed valve according to one embodiment of the invention.

FIG. 1 presents a disc structure which provides an embodiment of an acceleration-primed valve. In FIG. 1(a), a disc rotating around a centre or axis 100 with angular velocity W, rotating in the direction of the arrow, comprises a holding chamber 101 dimensioned to have an inner radial wall of radius R1 and outer radial wall of radius R2, an input channel 102 and output channel 103. An acceleration-primed valve system is illustrated comprising a capillary valve 104 and a goose-neck shaped outlet channel 105, which extends radially inward from the capillary valve, having an innermost portion that is radially outward, R3, of the innermost portion of the holding chamber, R1.

An optional capillary valve 106 at the output of the outlet channel may be used to control the time at which the fluid flow is delivered to the receiving chamber once the acceleration-primed capillary valve 104 is defeated or opened.

In FIG. 1(b), the disc rotates at an initial angular velocity W1. As illustrated, a liquid 110 in the holding chamber fills the outlet channel to the capillary valve at radius R4 through centrifugal force, but goes no further, as the centrifugal force generated by the angular velocity W1 has not opened or defeated the capillary valve 104. In other words the acceleration-primed capillary valve remains closed.

In FIG. 1(c), a rapid tangential acceleration drives fluid against the wall of the holding chamber nearest the outlet channel, i.e. the fluid is pushed against the side wall at a level above R4 shown in FIG. 1(c). The tangential acceleration is chosen such that the induced pressure transient is greater than the release pressure of the capillary valve on the outlet channel. This pressure transient can be approximated by the azimuthal acceleration multiplied by the circumferential extent, R2, of the liquid in the holding chamber and the density of the liquid, just as the pressure at the bottom of a chamber of liquid subject to gravity is gravitational acceleration multiplied by the depth of the chamber multiplied by the liquid density. As a result, the pressure transient defeats or opens the capillary valve to allow liquid pass through the goose-neck outlet channel as the liquid head in the holding chamber is at R1>R3.

This embodiment has the advantage of preventing inadvertent flow through the outlet channel at low angular velocity, thereby increasing the flexibility at which upstream microfluidic processes can be designed/controlled.

In one embodiment, the outlet channel may be a hydrophilic capillary channel in which case the fluid from the holding chamber advances via capillary force, once the capillary valve is opened or defeated. This is achieved by reducing the angular velocity of the disc to a speed where capillary force within the outlet channel is greater than centrifugal force exerted. This action primes the outlet channel, where after normal disc rotation may be resumed and the liquid flows through the goose-neck channel.

In another embodiment an output capillary valve 106 may be placed in the outlet channel to allow delivery of fluid at a time controlled by an angular velocity high enough to defeat or open the output capillary valve.

In another embodiment the outlet channel may be hydrophobic or sufficiently large to prevent capillary action defeating centrifugal force, since this acceleration-primed valve does not depend on capillary action to siphon liquid through the goose-neck once the capillary valve is defeated or opened.

Figure 2:
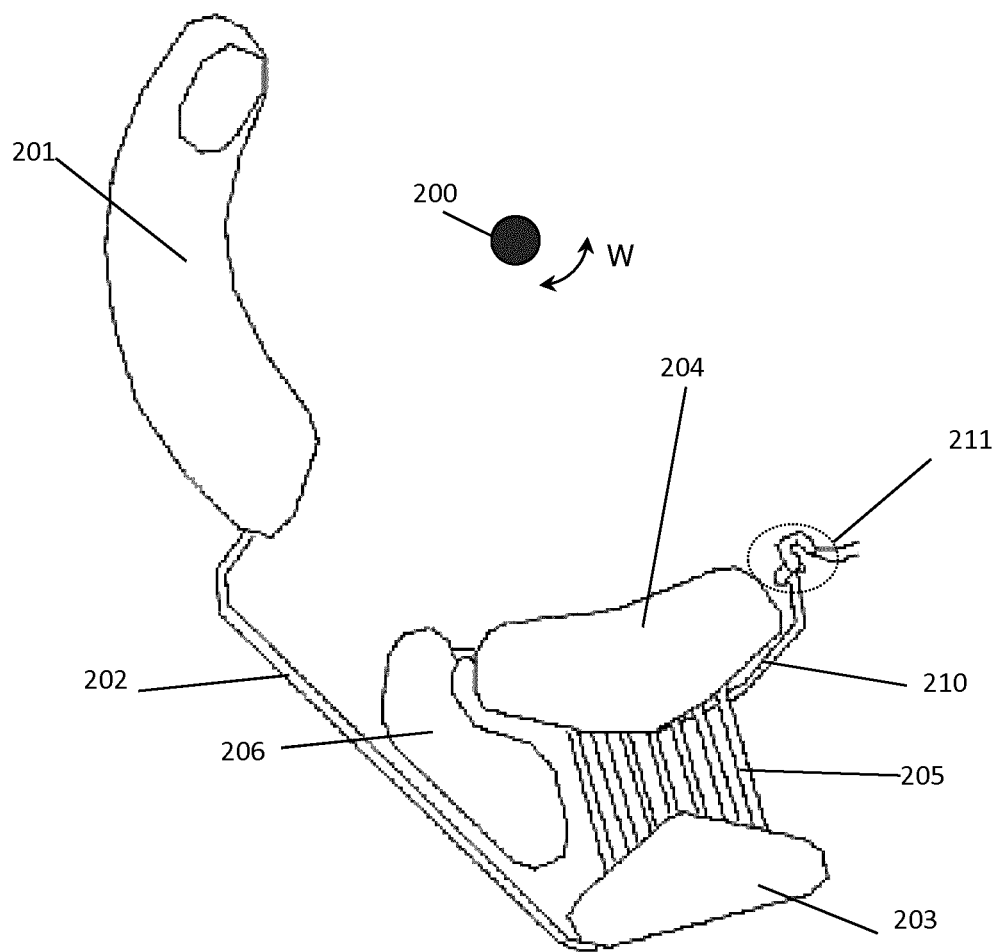
FIG. 2 illustrates an embodiment whereby the holding chamber is a dual-chambered plasma separation structure, with transport capillaries, connecting both chambers, used to dampen the re-suspension of cells into the plasma during the acceleration priming of said valves.

FIG. 2 illustrates an alternative embodiment of the invention in which the holding chamber is designed to perform a plasma separation of whole blood. Here, a disc rotates around a centre 200 with angular velocity W, and comprises an inlet chamber 201, wherein whole blood is applied. Upon rotation at angular velocity W1, the centrifugal force created transports this whole blood through the connecting channel 202 into a plasma separation structure comprising a cell holding chamber 203 connected to a plasma holding chamber 204 via transport capillary channels 205. Excess whole blood overflows into an overflow chamber 206, resulting in a fixed volume amount of whole blood transported to the plasma separation structure. The plasma holding chamber has an output channel 210 connected to a acceleration-primed valve 211, where after the fluid progresses to other downstream processing steps (not shown).

Upon transport of the whole blood into the plasma separation structure, the disc now increases its angular velocity to W2>>W1, whereby the plasma within the whole blood separates from the cell volume, using centrifugation principles understood to those skilled in the art. The size of the plasma holding and cell holding chambers are designed such that the interface between the separated plasma and cells is located at a radial distance within the transport capillaries or cell holding chamber. The radius of this interface depends on the mean cell volume within the whole blood specimen. The time taken by the plasma separation process is much reduced by selecting the angular velocity W2 at rates over 7,000 RPM. At such speeds, there are limits to the practical and cost-effective use of capillary valves for retention of such fluids with channels in the 100-200 um dimension. Hence, the use of an acceleration-primed valve.

In typical plasma separation structures, tangential flow gradients produced by the acceleration profile required to defeat or open such a valve tends to agitate the separated cell volume, thereby resuspending the cells into the plasma. This embodiment improves upon the art, by having two separate structures connected by narrow transport capillaries. The transport capillaries have the effect of damping down the agitated cells, limiting their resuspension into the plasma holding chamber.

The embodiments in the invention described with reference to the drawings comprise a computer apparatus and/or processes performed in a computer apparatus. However, the invention also extends to computer programs, particularly computer programs stored on or in a carrier adapted to bring the invention into practice. The program may be in the form of source code, object code, or a code intermediate source and object code, such as in partially compiled form or in any other form suitable for use in the implementation of the method according to the invention. The carrier may comprise a storage medium such as ROM, e.g. CD ROM, or magnetic recording medium, e.g. a floppy disk or hard disk. The carrier may be an electrical or optical signal which may be transmitted via an electrical or an optical cable or by radio or other means.

In the specification the terms "comprise, comprises, comprised and comprising" or any variation thereof and the terms include, includes, included and including" or any variation thereof are considered to be totally interchangeable and they should all be afforded the widest possible interpretation and vice versa.

The invention is not limited to the embodiments hereinbefore described but may be varied in both construction and detail.

The invention claimed is:

1. A microfluidic system for processing biological samples comprising:
a holding chamber adapted for holding a fluid and to be rotated on a platform about a central axis, wherein the holding chamber is dimensioned to have an inner radial wall of radius (R1) and outer radial wall of radius (R2) from the central axis, said holding chamber comprising an outlet through which fluid flow is controlled by an acceleration-primed valve system, wherein the acceleration-primed valve system comprises a capillary valve and an outlet channel, the capillary valve comprising an innermost portion that is radially inward, (R3), of the outermost portion of the holding chamber, (R2), and wherein the capillary valve is primed by a force generated by a tangential acceleration of the platform.

2. The microfluidic system of claim 1, further wherein the capillary valve comprises an innermost portion that is radially outward, (R3), of the innermost portion of the holding chamber, (R1).

3. The microfluidic system of claim 2 wherein on rotating the platform about the central axis at a first speed the fluid in the holding chamber is pushed against the capillary valve at the radius (R3) such that the fluid remains in the holding chamber.

4. The microfluidic system of claim 2 wherein on rotating the platform about the central axis at a first speed the fluid in the holding chamber is pushed against the capillary valve at the radius (R3) such that the fluid remains in the holding chamber and the platform is adapted to be rotated at a second speed such that the tangential acceleration is chosen such that an induced pressure transient is greater than a release pressure of the capillary valve to enable fluid flow to the outlet channel.

5. The microfluidic system of claim 1 wherein the capillary valve is opened by applying sufficient rotation speed to the platform.

6. The microfluidic system of claim 1 wherein the outlet channel extends radially inwardly and having an innermost portion that is radially outward of an innermost portion of the holding chamber.

7. The microfluidic system of claim 1 wherein the outlet channel is dimensioned in a goose-neck type shape.

8. The microfluidic system of claim 1 wherein the outlet channel comprises a hydrophilic capillary channel adapted to allow the fluid from the holding chamber to flow into the outlet channel via capillary force, when the capillary valve is opened.

9. The microfluidic system of claim 8 wherein the fluid is allowed to flow into the outlet channel by reducing an angular velocity of the platform to a speed such that the capillary force within the outlet channel is greater than a centrifugal force exerted on the holding chamber.

10. The microfluidic system of claim 1 comprising a second capillary valve adapted to allow delivery of the fluid at a time controlled by an angular velocity high enough to open the output capillary valve.

11. A microfluidic system for separating plasma within whole blood comprising:
 a platform coupled to a rotary motor;
 a plasma holding chamber connected to a cell holding chamber radially outward of the plasma holding chamber, wherein said connection comprises a plurality of transport capillary channels, the plasma holding chamber adapted to be rotated on the platform about a central axis, wherein the plasma holding chamber is dimensioned to have an inner radial wall of radius (R1) and outer radial wall of radius (R2) from the central axis, and wherein the plasma holding chamber further has an output channel connected to an acceleration primed valve, wherein the acceleration-primed valve comprises a valve and an outlet channel, the valve comprising an innermost portion that is radially inward, (R3), of the outermost portion of the holding chamber, (R2), and wherein the valve is primed by a force generated by a tangential acceleration of the platform.

12. The microfluidic system of claim 11 wherein at least one of the transport capillaries is adapted to dampen down agitated cells in the blood limiting their re-suspension into the plasma holding chamber.

13. The microfluidic system of claim 11 wherein said system is used for the separation of any particles in solution.

14. A microfluidic system for processing biological samples comprising:
 a holding chamber adapted for holding a fluid and to be rotated on a platform about a central axis, wherein the holding chamber is dimensioned to have an inner radial wall of radius (R1) and outer radial wall of radius (R2) from the central axis, said holding chamber comprising an outlet through which fluid flow is controlled by an acceleration-primed valve system, wherein the acceleration-primed valve system comprises a valve and an outlet channel, the valve comprising an innermost portion that is radially inward, (R3), of the outermost portion of the holding chamber, (R2), and wherein the valve is primed by a force generated by a tangential acceleration of the platform.

* * * * *